United States Patent
Santra et al.

(10) Patent No.: US 11,125,869 B2
(45) Date of Patent: Sep. 21, 2021

(54) ESTIMATING ANGLE OF HUMAN TARGET USING MMWAVE RADAR

(71) Applicant: Infineon Technologies AG, Neubiberg (DE)

(72) Inventors: Avik Santra, Munich (DE); Assad Ali, Munich (DE)

(73) Assignee: Infineon Technologies AG, Neubiberg (DE)

( * ) Notice: Subject to any disclaimer, the term of this patent is extended or adjusted under 35 U.S.C. 154(b) by 324 days.

(21) Appl. No.: 16/162,144

(22) Filed: Oct. 16, 2018

(65) Prior Publication Data

US 2020/0116850 A1 Apr. 16, 2020

(51) Int. Cl.
G01S 13/44 (2006.01)
G01S 13/50 (2006.01)
G01S 13/72 (2006.01)

(52) U.S. Cl.
CPC .......... *G01S 13/449* (2013.01); *G01S 13/505* (2013.01); *G01S 13/72* (2013.01)

(58) Field of Classification Search
CPC ....... G01S 13/449; G01S 13/505; G01S 13/72
USPC ........................................................ 342/149
See application file for complete search history.

(56) References Cited

U.S. PATENT DOCUMENTS

| 4,241,347 A | 12/1980 | Albanese et al. |
| 4,549,184 A * | 10/1985 | Boles ........................ F41G 5/18 342/25 B |
| 6,147,572 A | 11/2000 | Kaminski et al. |
| 6,414,631 B1 | 7/2002 | Fujimoto |

(Continued)

FOREIGN PATENT DOCUMENTS

| CN | 1463161 A | 12/2003 |
| CN | 1716695 A | 1/2006 |

(Continued)

OTHER PUBLICATIONS

Infineon, "Using BGT24MTR11 in Low Power Applications", BGT24MTR11, 24 Ghz Radar, RF and Protection Devices, Application Note AN341, Revision: Rev. 1.0, Dec. 2, 2013, 25 pages.

Tanis, S., "Automotive Radar Sensors and Congested Radio Spectrum: An Urban Electronic Battlefield?", Analog Devices, Analog Dialogue, Jul. 2018, 5 pages.

Texas Instruments, "XWR1xxx Power Management Optimizations— Low Cost LC Filter Solution", Application Report SWRA577— Oct. 2017, 19 pages.

(Continued)

*Primary Examiner* — Peter M Bythrow
*Assistant Examiner* — Nuzhat Pervin
(74) *Attorney, Agent, or Firm* — Slater Matsil, LLP

(57) ABSTRACT

A method of estimating an angle of arrival of a radar signal reflected on a human target includes: receiving the reflected radar signal with first and second antennas of a millimeter-wave radar; transforming the reflected radar signal received to generate first and second range spectrum, respectively; generating a first and second range-Doppler maps based on the first and second range spectrum, respectively; determining or estimating a Doppler velocity based on the first range-Doppler map or the second range-Doppler map; compensating the first and second range-Doppler maps by selecting a peak in the first or second range-Doppler maps based on the determined Doppler velocity; identifying an index of the first macro-compensated range-Doppler map corresponding to an identified target; estimating a phase difference based on the first and second macro-compensated range-Doppler maps and the identified index; and estimating the angle of arrival based on the phase difference.

31 Claims, 8 Drawing Sheets

(56) References Cited

U.S. PATENT DOCUMENTS

| | | | |
|---|---|---|---|
| 6,538,599 B1* | 3/2003 | David | G01S 7/2926 |
| | | | 342/104 |
| 6,636,174 B2 | 10/2003 | Arikan et al. | |
| 7,048,973 B2 | 5/2006 | Sakamoto et al. | |
| 7,057,564 B2 | 6/2006 | Tsai et al. | |
| 7,171,052 B2 | 1/2007 | Park | |
| 7,317,417 B2 | 1/2008 | Arikan et al. | |
| 7,596,241 B2 | 9/2009 | Rittscher et al. | |
| 7,692,574 B2 | 4/2010 | Nakagawa | |
| 7,873,326 B2 | 1/2011 | Sadr | |
| 7,889,147 B2 | 2/2011 | Tam et al. | |
| 8,228,382 B2 | 7/2012 | Pattikonda | |
| 8,497,805 B2 | 7/2013 | Rofougaran et al. | |
| 8,659,369 B2 | 2/2014 | Rofougaran et al. | |
| 8,731,502 B2 | 5/2014 | Salle et al. | |
| 8,836,596 B2 | 9/2014 | Richards et al. | |
| 8,847,814 B2 | 9/2014 | Himmelstoss et al. | |
| 8,860,532 B2 | 10/2014 | Gong et al. | |
| 8,976,061 B2 | 3/2015 | Chowdhury | |
| 9,172,132 B2 | 10/2015 | Kam et al. | |
| 9,182,476 B2 | 11/2015 | Wintermantel | |
| 9,202,105 B1 | 12/2015 | Wang et al. | |
| 9,229,102 B1* | 1/2016 | Wright | G01S 13/887 |
| 9,413,079 B2 | 8/2016 | Kamgaing et al. | |
| 9,435,884 B2* | 9/2016 | Inoue | G01S 13/346 |
| 9,495,600 B2 | 11/2016 | Heu et al. | |
| 9,869,760 B2* | 1/2018 | Park | G01S 13/04 |
| 9,886,095 B2 | 2/2018 | Pothier | |
| 9,935,065 B1 | 4/2018 | Baheti et al. | |
| 9,939,524 B2* | 4/2018 | Winstead | G01S 13/18 |
| 10,145,954 B2* | 12/2018 | Davis | G01S 13/878 |
| 10,264,996 B2* | 4/2019 | Kiaei | A61B 5/0205 |
| 10,641,885 B2* | 5/2020 | Frick | G01S 13/588 |
| 10,746,852 B2* | 8/2020 | Adib | A61B 5/08 |
| 2003/0179127 A1 | 9/2003 | Wienand | |
| 2004/0238857 A1 | 12/2004 | Beroz et al. | |
| 2005/0179579 A1 | 8/2005 | Pinder et al. | |
| 2006/0001572 A1 | 1/2006 | Gaucher et al. | |
| 2006/0049995 A1 | 3/2006 | Imaoka et al. | |
| 2006/0067456 A1 | 3/2006 | Ku et al. | |
| 2007/0210959 A1 | 9/2007 | Herd et al. | |
| 2008/0106460 A1* | 5/2008 | Kurtz | G01S 13/34 |
| | | | 342/99 |
| 2008/0238759 A1 | 10/2008 | Carocari et al. | |
| 2008/0291115 A1 | 11/2008 | Doan et al. | |
| 2008/0308917 A1 | 12/2008 | Pressel et al. | |
| 2009/0073026 A1 | 3/2009 | Nakagawa | |
| 2009/0085815 A1 | 4/2009 | Jakab et al. | |
| 2009/0153428 A1 | 6/2009 | Rofougaran et al. | |
| 2009/0315761 A1 | 12/2009 | Walter et al. | |
| 2010/0207805 A1 | 8/2010 | Haworth | |
| 2011/0102242 A1* | 5/2011 | Takeya | G01S 7/35 |
| | | | 342/105 |
| 2011/0299433 A1 | 12/2011 | Darabi et al. | |
| 2012/0087230 A1 | 4/2012 | Guo et al. | |
| 2012/0092284 A1 | 4/2012 | Rofougaran et al. | |
| 2012/0116231 A1 | 5/2012 | Liao et al. | |
| 2012/0139777 A1* | 6/2012 | Hunter | G01S 13/5244 |
| | | | 342/175 |
| 2012/0195161 A1 | 8/2012 | Little et al. | |
| 2012/0206339 A1 | 8/2012 | Dahl | |
| 2012/0223855 A1* | 9/2012 | Kurono | G01S 7/2925 |
| | | | 342/146 |
| 2012/0265486 A1 | 10/2012 | Klofer et al. | |
| 2012/0268314 A1 | 10/2012 | Kuwahara et al. | |
| 2012/0280900 A1 | 11/2012 | Wang et al. | |
| 2013/0027240 A1 | 1/2013 | Chowdhury | |
| 2013/0106673 A1 | 5/2013 | McCormack et al. | |
| 2013/0194128 A1* | 8/2013 | Van Der Merwe | H01Q 19/06 |
| | | | 342/107 |
| 2014/0028542 A1 | 1/2014 | Lovitt et al. | |
| 2014/0070994 A1 | 3/2014 | Schmalenberg et al. | |
| 2014/0145883 A1 | 5/2014 | Baks et al. | |
| 2014/0324888 A1 | 10/2014 | Xie et al. | |
| 2015/0070204 A1* | 3/2015 | Shirakawa | G01S 13/34 |
| | | | 342/90 |
| 2015/0160335 A1* | 6/2015 | Lynch | G01S 13/4418 |
| | | | 342/194 |
| 2015/0181840 A1 | 7/2015 | Tupin, Jr. et al. | |
| 2015/0185316 A1 | 7/2015 | Rao et al. | |
| 2015/0198709 A1* | 7/2015 | Inoue | G01S 13/52 |
| | | | 342/147 |
| 2015/0212198 A1 | 7/2015 | Nishio et al. | |
| 2015/0243575 A1 | 8/2015 | Strothmann et al. | |
| 2015/0277569 A1 | 10/2015 | Sprenger et al. | |
| 2015/0325925 A1 | 11/2015 | Kamgaing et al. | |
| 2015/0346820 A1 | 12/2015 | Poupyrev et al. | |
| 2015/0348821 A1 | 12/2015 | Iwanaga et al. | |
| 2015/0364816 A1 | 12/2015 | Murugan et al. | |
| 2016/0018511 A1 | 1/2016 | Nayyar et al. | |
| 2016/0041617 A1 | 2/2016 | Poupyrev | |
| 2016/0041618 A1 | 2/2016 | Poupyrev | |
| 2016/0061942 A1 | 3/2016 | Rao et al. | |
| 2016/0061947 A1 | 3/2016 | Patole et al. | |
| 2016/0098089 A1 | 4/2016 | Poupyrev | |
| 2016/0103213 A1 | 4/2016 | Ikram et al. | |
| 2016/0109566 A1 | 4/2016 | Liu et al. | |
| 2016/0118353 A1 | 4/2016 | Ahrens et al. | |
| 2016/0135655 A1 | 5/2016 | Ahn et al. | |
| 2016/0146931 A1 | 5/2016 | Rao et al. | |
| 2016/0146933 A1 | 5/2016 | Rao et al. | |
| 2016/0178730 A1 | 6/2016 | Trotta et al. | |
| 2016/0187462 A1 | 6/2016 | Altus et al. | |
| 2016/0191232 A1 | 6/2016 | Subburaj et al. | |
| 2016/0200276 A1* | 7/2016 | Diewald | G01S 13/56 |
| | | | 342/28 |
| 2016/0223651 A1 | 8/2016 | Kamo et al. | |
| 2016/0223665 A1* | 8/2016 | Winstead | G01S 13/585 |
| 2016/0240907 A1 | 8/2016 | Haroun | |
| 2016/0249133 A1 | 8/2016 | Sorensen | |
| 2016/0252607 A1 | 9/2016 | Saboo et al. | |
| 2016/0259037 A1 | 9/2016 | Molchanov et al. | |
| 2016/0266233 A1 | 9/2016 | Mansour | |
| 2016/0269815 A1 | 9/2016 | Liao et al. | |
| 2016/0291130 A1 | 10/2016 | Ginsburg et al. | |
| 2016/0299215 A1 | 10/2016 | Dandu et al. | |
| 2016/0306034 A1 | 10/2016 | Trotta et al. | |
| 2016/0320852 A1 | 11/2016 | Poupyrev | |
| 2016/0320853 A1 | 11/2016 | Lien et al. | |
| 2016/0327633 A1 | 11/2016 | Kumar et al. | |
| 2016/0334502 A1 | 11/2016 | Ali et al. | |
| 2016/0349363 A1* | 12/2016 | Millar | G01S 13/449 |
| 2016/0349845 A1 | 12/2016 | Poupyrev et al. | |
| 2016/0371849 A1* | 12/2016 | Pavek | G01S 7/414 |
| 2017/0033062 A1 | 2/2017 | Liu et al. | |
| 2017/0045607 A1 | 2/2017 | Bharadwaj et al. | |
| 2017/0052618 A1 | 2/2017 | Lee et al. | |
| 2017/0054449 A1 | 2/2017 | Mani et al. | |
| 2017/0060254 A1 | 3/2017 | Molchanov et al. | |
| 2017/0070952 A1 | 3/2017 | Balakrishnan et al. | |
| 2017/0074974 A1 | 3/2017 | Rao et al. | |
| 2017/0074980 A1 | 3/2017 | Adib et al. | |
| 2017/0090014 A1 | 3/2017 | Subburaj et al. | |
| 2017/0090015 A1 | 3/2017 | Breen et al. | |
| 2017/0115377 A1 | 4/2017 | Giannini et al. | |
| 2017/0131395 A1 | 5/2017 | Reynolds et al. | |
| 2017/0139036 A1 | 5/2017 | Nayyar et al. | |
| 2017/0141453 A1 | 5/2017 | Waelde et al. | |
| 2017/0170947 A1 | 6/2017 | Yang | |
| 2017/0176574 A1 | 6/2017 | Eswaran et al. | |
| 2017/0192847 A1 | 7/2017 | Rao et al. | |
| 2017/0201019 A1 | 7/2017 | Trotta | |
| 2017/0212597 A1 | 7/2017 | Mishra | |
| 2017/0356991 A1* | 12/2017 | Yosoku | G01S 13/931 |
| 2017/0364160 A1 | 12/2017 | Malysa et al. | |
| 2018/0045819 A1* | 2/2018 | Cornic | G01S 13/36 |
| 2018/0046255 A1 | 2/2018 | Rothera et al. | |
| 2018/0071473 A1 | 3/2018 | Trotta et al. | |
| 2018/0100918 A1* | 4/2018 | Davis | G01S 13/87 |
| 2018/0101239 A1 | 4/2018 | Yin et al. | |
| 2018/0136324 A1* | 5/2018 | Klotzbuecher | G01S 13/343 |
| 2018/0329054 A1* | 11/2018 | Pokrass | G01S 7/2923 |
| 2019/0025420 A1* | 1/2019 | Frick | G01S 13/588 |

(56) References Cited

U.S. PATENT DOCUMENTS

| | | | | |
|---|---|---|---|---|
| 2019/0324107 | A1* | 10/2019 | Robinson | G01S 13/933 |
| 2019/0346548 | A1* | 11/2019 | Barkan | G01S 13/89 |
| 2019/0377062 | A1* | 12/2019 | Barkan | G01S 7/2925 |
| 2020/0049810 | A1* | 2/2020 | Longman | G01S 13/282 |

FOREIGN PATENT DOCUMENTS

| | | |
|---|---|---|
| CN | 101490578 A | 7/2009 |
| CN | 101585361 A | 11/2009 |
| CN | 102788969 A | 11/2012 |
| CN | 102967854 A | 3/2013 |
| CN | 103529444 A | 1/2014 |
| CN | 203950036 U | 11/2014 |
| DE | 102008054570 A1 | 6/2010 |
| DE | 102010045980 A1 | 5/2011 |
| DE | 102011100907 A1 | 1/2012 |
| DE | 102011075725 A1 | 11/2012 |
| DE | 102014118063 A1 | 7/2015 |
| GB | 2247799 A | 3/1992 |
| JP | 2001174539 A | 6/2001 |
| JP | 2004198312 A | 7/2004 |
| JP | 2006234513 A | 9/2006 |
| JP | 2008029025 A | 2/2008 |
| JP | 2008089614 A | 4/2008 |
| JP | 2009069124 A | 4/2009 |
| JP | 2011529181 A | 12/2011 |
| JP | 2012112861 A | 6/2012 |
| JP | 2013521508 A | 6/2013 |
| JP | 2014055957 A | 3/2014 |
| KR | 20090063166 A | 6/2009 |
| KR | 20140082815 A | 7/2014 |
| WO | 2007060069 A1 | 5/2007 |
| WO | 2013009473 A2 | 1/2013 |
| WO | 2016033361 A1 | 3/2016 |

OTHER PUBLICATIONS

Texas Instruments, "Programming Chirp Parameters in TI Radar Devices", Application Report SWRA553—May 2017, 15 pages.

Chen, Xiaolong et al., "Detection and Extraction of Marine Target with Micromotion via Short-Time Fractional Fourier Transform in Sparse Domain," IEEE International Conference on Signal Processing, Communications and Computing, ICSPCC, Aug. 5-8, 2016, 5 pages.

Chen, X. et al., "Detection and Extraction of Target With Micromotion in Spiky Sea Clutter via Short-Time Fractional Fourier Transform", IEEE Transactions on Geoscience and Remote Sensing, vol. 52, No. 2, Feb. 2014, pp. 1002-1018.

Chuanhua, Du, "FMCW Radar Range-Doppler Processing and Beam Formation Technology," Chinese Doctoral Dissertations & Master's Theses Full Text Database (Masters)—Information Science and Technology Series, China National Knowledge Infrastructure, ISSN 1674-0246, CN 11-9144/G, Dec. 16, 2004-Mar. 2015, 14 pages.

Deacon, Peter et al., "Frequency Modulated Continuous Wave (FMCW) Radar," Design Team 6 Technical Lecture, Nov. 9, 2011, 27 pages.

Diederichs, Kailtyn et al., "Wireless Biometric Individual Identification Utilizing Millimeter Waves", IEEE Sensors Letters, vol. 1, No. 1, IEEE Sensors Council 3500104, Feb. 2017, 4 pages.

Dooring Alert Systems, "Riders Matter," http:\\dooringalertsystems.com, printed Oct. 4, 2017, 16 pages.

Filippelli, Mario et al., "Respiratory dynamics during laughter," J Appl Physiol, (90), 1441-1446, Apr. 2001, http://jap.physiology.org/content/jap/90/4/1441.full.pdf.

Fox, Ben, "The Simple Technique That Could Save Cyclists' Lives," https://www.outsideonline.com/2115116/simple-technique-could-save-cyclists-lives, Sep. 19, 2016, 6 pages.

Gu, Changzhan et al., "Assessment of Human Respiration Patterns via Noncontact Sensing Using Doppler Multi-Radar System", Sensors Mar. 2015, 15(3), 6383-6398, doi: 10.3390/s150306383, 17 pages.

Guercan, Yalin "Super-resolution Algorithms for Joint Range-Azimuth-Doppler Estimation in Automotive Radars," Technische Universitet Delft, TUDelft University of Technology Challenge the Future, Jan. 25, 2017, 72 pages.

Inac, Ozgur et al., "A Phased Army RFIC with Built-In Self-Test Capabilities," IEEE Transactions on Microwave Theory and Techniques, vol. 60, No. 1, Jan. 2012, 10 pages.

Kizhakkel, V., "Pulsed Radar Target Recognition Based on Micro-Doppler Signatures Using Wavelet Analysis", A Thesis, Graduate Program in Electrical and Computer Engineering, Ohio State University, Jan. 2013-May 2013, 118 pages.

Kuehnke, Lutz, "Phased Array Calibration Procedures Based on Measured Element Patterns," 2001 Eleventh International Conference on Antennas and Propagation, IEEE Conf., Publ. No. 480, Apr. 17-20, 2001, 4 pages.

Lange, O. et al., "Optimization of array geometry for direction-of-arrival estimation using a priori information", Adv. Radio Sci., 8, Feb. 2010, pp. 87-94.

Lim, Soo-Chul et al., "Expansion of Smartwatch Touch Interface from Touchscreen to Around Device Interface Using Infrared Line Image Sensors," Sensors 2015, ISSN 1424-8220, vol. 15, 16642-16653, doi:10.3390/s150716642, www.mdpi.com./journal/sensors, Jul. 15, 2009, 12 pages.

Lin, Jau-Jr et al., "Design of an FMCW radar baseband signal processing system for automotive application," SpringerPlus a SpringerOpen Journal, (2016) 5:42, http://creativecommons.org/licenses/by/4.0/, DOI 10.1186/s40064-015-1583-5; Jan. 2016, 16 pages.

Microwave Journal Frequency Matters, "Single-Chip 24 GHz Radar Front End," Infineon Technologies AG, www.microwavejournal.com/articles/print/21553-single-chip-24-ghz-radar-front-end, Feb. 13, 2014, 2 pages.

Wikipedia, "Monopulse radar", https://en.wikipedia.org/wiki/Monopulse_radar, Sep. 3, 2018, 6 pages.

Wikipedia, "Phase-comparison monopulse", https://en.wikipedia.org/wiki/Phase-comparison_monopulse, Sep. 3, 2018, 3 pages.

Richards, Mark A., "Fundamentals of Radar Signal Processing," McGraw Hill Electronic Engineering, ISBN: 0-07-144474-2, Jun. 2005, 93 pages.

Schroff, Florian et al., "FaceNet: A Unified Embedding for Face Recognition and Clustering," CVF, CVPR2015, IEEE Computer Society Conference on Computer Vision and Pattern Recognition; Mar. 12, 2015, pp. 815-823.

Simon, W., et al., "Highly Integrated KA-Band Tx Frontend Module Including 8x8 Antenna Array," IMST GmbH, Germany, Asia Pacific Microwave Conference, Dec. 7-10, 2009, 63 pages.

Suleymanov, Suleyman, "Design and Implementation of an FMCW Radar Signal Processing Module for Automotive Applications," Master Thesis, University of Twente, Aug. 31, 2016, 61 pages.

Thayananthan, T. et al., "Intelligent target recognition using micro-Doppler radar signatures," Defence R&D Canada, Radar Sensor Technology III, Proc. of SPIE, vol. 7308, 730817, Dec. 9, 2009, 11 pages.

Thayaparan, T. et al., "Micro-Doppler Radar Signatures for Intelligent Target Recognition," Defence Research and Development Canada, Technical Memorandum, DRDC Ottawa TM 2004-170, Sep. 2004, 73 pages.

Wilder, Carol N., et al., "Respiratory patterns in infant cry," Canada Journal of Speech, Human Communication Winter, 1974-75, http://cjslpa.ca/files/1974_HumComm_Vol_01/No_03_2-60/Wilder_Baken_HumComm_1974.pdf, pp. 18-34.

Xin, Qin et al., "Signal Processing for Digital Beamforming FMCW SAR," Hindawi Publishing Corporation, Mathematical Problems in Engineering, vol. 2014, Article ID 859890, http://dx.doi.org/10.1155/2014/859890, 11 pages.

Chen, Victor C., "Advances in Applications of Radar Micro-Doppler Signatures", IEEE Conference on Antenna Measurements & Applications (CAMA), Nov. 16-19, 2014, 4 pages.

\* cited by examiner

ESTIMATING ANGLE OF HUMAN TARGET USING MMWAVE RADAR

TECHNICAL FIELD

The present invention relates generally to an electronic system and method, and, in particular embodiments, to estimating angle of human target using a millimeter-wave (mmWave) radar.

BACKGROUND

Applications in the millimeter-wave frequency regime have gained significant interest in the past few years due to the rapid advancement in low cost semiconductor technologies, such as silicon germanium (SiGe) and fine geometry complementary metal-oxide semiconductor (CMOS) processes. Availability of high-speed bipolar and metal-oxide semiconductor (MOS) transistors has led to a growing demand for integrated circuits for millimeter-wave applications at 24 GHz, 60 GHz, 77 GHz, and 80 GHz and also beyond 100 GHz. Such applications include, for example, automotive radar systems and multi-gigabit communication systems.

In some radar systems, the distance between the radar and a target is determined by transmitting a frequency modulated signal, receiving a reflection of the frequency modulated signal (also referred to as the echo), and determining a distance based on a time delay and/or frequency difference between the transmission and reception of the frequency modulated signal. Accordingly, some radar systems include a transmit antenna to transmit the radio-frequency (RF) signal, and a receive antenna to receive the reflected RF signal, as well as the associated RF circuitry used to generate the transmitted signal and to receive the RF signal. In some cases, multiple antennas may be used to implement directional beams using phased array techniques. A multiple-input and multiple-output (MIMO) configuration with multiple chipsets can be used to perform coherent and non-coherent signal processing as well.

SUMMARY

In accordance with an embodiment, a method of estimating an angle of arrival of a radar signal reflected on a human target includes: receiving the reflected radar signal with first and second antennas of a millimeter-wave radar; transforming the reflected radar signal received with the first and second antennas to generate first and second range spectrum, respectively; generating a first range-Doppler map based on the first range spectrum; generating a second range-Doppler map based on the second range spectrum; determining or estimating a Doppler velocity based on the first range-Doppler map or the second range-Doppler map; macro-compensating the first range-Doppler map and the second range-Doppler map by selecting a peak in the first range-Doppler map or the second range-Doppler map based on the determined Doppler velocity; identifying an index of the first macro-compensated range-Doppler map corresponding to an identified target; estimating a phase difference based on the first and second macro-compensated range-Doppler maps and the identified index; and estimating the angle of arrival based on the phase difference.

In accordance with an embodiment, a millimeter-wave radar includes: first and second receiving antennas configured to receive a reflected radar signal, and a controller. The controller is configured to: transform the reflected radar signal received with the first and second receiving antennas to generate first and second range spectrum, respectively; generate a first range-Doppler map based on the first range spectrum; generate a second range-Doppler map based on the second range spectrum; determine or estimate a Doppler velocity based on the first range-Doppler map or the second range-Doppler map; compensate the first range-Doppler map and the second range-Doppler map by selecting a peak in the first range-Doppler map or the second range-Doppler map based on the determined Doppler velocity; identify an index of the first macro-compensated range-Doppler map corresponding to an identified target; estimate a phase difference based on the first and second macro-compensated range-Doppler maps and the identified index; and estimate an angle of arrival of the reflected signal based on the phase difference.

In accordance with an embodiment, a method of estimating an angle of arrival of a radar signal reflected on a human target includes: transmitting a radar signal towards the human target using a millimeter-wave radar, the transmitted radar signal including a sequence of pulses; receiving the reflected radar signal with first and second antennas of a millimeter-wave radar; determining a range of the human target based on the reflected signal; determining a Doppler velocity of the human target based on the reflected radar signal and the determined range of the human target; generating first and second compensated range-Doppler maps based on the reflected radar signal, the determined range of the human target, and the determined Doppler velocity; identifying an index of the first compensated range-Doppler map corresponding to an identified target; estimating a phase difference based on the first and second compensated range-Doppler maps and the identified index; and estimating the angle of arrival based on the phase difference.

BRIEF DESCRIPTION OF THE DRAWINGS

For a more complete understanding of the present invention, and the advantages thereof, reference is now made to the following descriptions taken in conjunction with the accompanying drawings, in which.

Corresponding numerals and symbols in different figures generally refer to corresponding parts unless otherwise indicated. The figures are drawn to clearly illustrate the relevant aspects of the preferred embodiments and are not necessarily drawn to scale.

DETAILED DESCRIPTION OF ILLUSTRATIVE EMBODIMENTS

The making and using of the embodiments disclosed are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The description below illustrates the various specific details to provide an in-depth understanding of several example embodiments according to the description. The embodiments may be obtained without one or more of the specific details, or with other methods, components, materials and the like. In other cases, known structures, materials or operations are not shown or described in detail so as not to obscure the different aspects of the embodiments. References to "an embodiment" in this description indicate that a particular configuration, structure or feature described in relation to the embodiment is included in at least one embodiment. Consequently, phrases such as "in one embodiment" that may appear at different points of the present description do not necessarily refer exactly to the same embodiment. Furthermore, specific formations, structures or features may be combined in any appropriate manner in one or more embodiments.

The present invention will be described with respect to embodiments in a specific context, a method of determining the angle of arrival of radar signals reflected from humans using a millimeter-wave radar having at least two receiving antennas and operating as a frequency-modulated continuous-wave (FMCW) radar. Embodiments of the present invention may be extended to other types of radars, such as pulsed radars.

In an embodiment of the present invention, estimating the angle of arrival of a radar signal reflected in a human is improved by compensating for Doppler components before calculating the angle of arrival using a phase mono-pulse algorithm. The macro-Doppler component of a moving human is subtracted from a range-Doppler map before estimating the angle of arrival. For static humans, Doppler components associated with vital signs (e.g., breathing) are compensated before estimating the angle of arrival.

Figure 1:
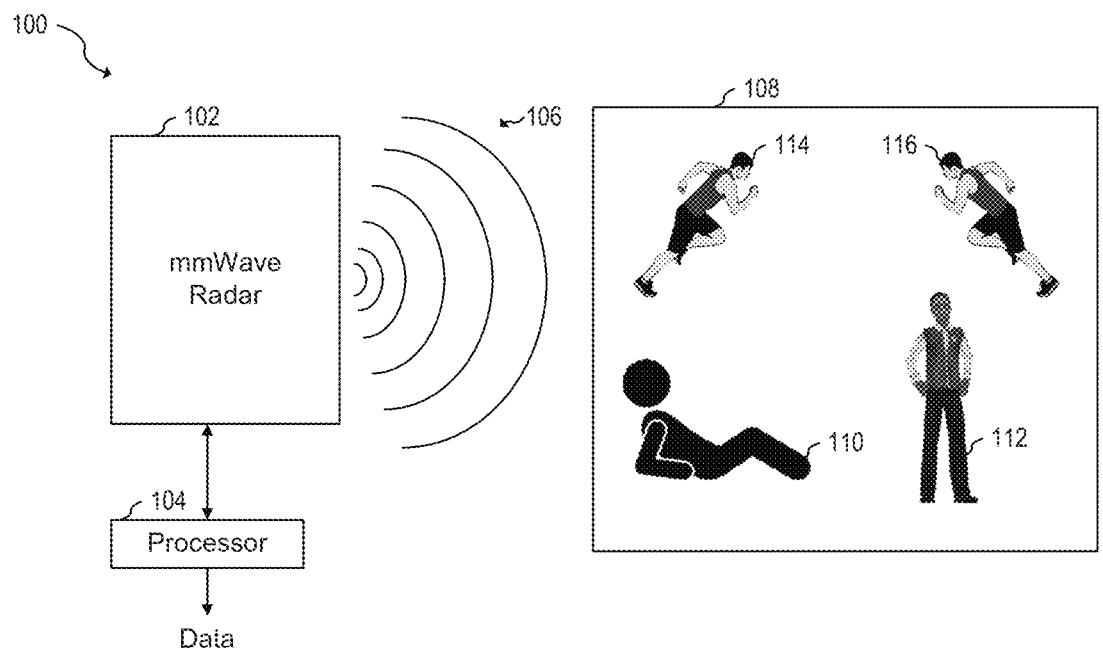
FIG. 1 shows a radar system, according to an embodiment of the present invention.

A millimeter-wave radar may be used to determine the angle of arrival of radar signals reflected in a human. For example, FIG. 1 shows radar system 100, according to an embodiment of the present invention. Radar system 100 includes millimeter-wave radar 102 and processor 104.

During normal operation, millimeter-wave radar 102 transmits a plurality of radiation pulses 106, such as chirps, towards scene 108. In some embodiments the chirps are linear chirps (i.e., the instantaneous frequency of the chirp varies linearly with time).

The transmitted radiation pulses 106 are reflected by objects in scene 108. The reflected radiation pulses (not shown in FIG. 1), which are also referred to as the echo signal, are detected by millimeter-wave radar 102 and processed by processor 104 to, for example, determine the angle of arrival of the echo signal.

The objects in scene 108 may include static humans, such as lying human 110, humans exhibiting low and infrequent motions, such as standing human 112, and moving humans, such as running or walking human 114 and 116. The objects in scene 108 may also include static objects, such as furniture and periodic movement equipment (not shown). Other objects may also be present in scene 108.

Processor 104 analyses the echo data to determine the location of humans using signal processing techniques. For example, in some embodiments, a range FFT is used for estimating the range component of the location of a detected human (i.e., how far is the human from the millimeter-wave radar). The azimuth component of the location of the detected human may be determined using angle estimation techniques.

Processor 104 may be implemented as a general purpose processor, controller or digital signal processor (DSP) that includes, for example, combinatorial circuits coupled to a memory. In some embodiments, the DSP may be implemented with an ARM architecture, for example. In some embodiments, processor 104 may be implemented as a custom application specific integrated circuit (ASIC). In some embodiments, processor 104 includes a plurality of processors, each having one or more processing cores. In other embodiments, processor 104 includes a single processor having one or more processing cores. Other implementations are also possible. For example, some embodiments may implement decoder 302 using software running in a general purpose micro-controller or processor having, for example, a CPU coupled to a memory and implemented with an ARM or x86 architecture. Some embodiments may be implemented as a combination of hardware accelerator and software running on a DSP or general purpose microcontroller.

Millimeter-wave radar 102 operates as a FMCW radar that includes a millimeter-wave radar sensor circuit, a transmitting antenna, and at least two receiving antennas. Millimeter-wave radar 102 transmits and receives signals in the 20 GHz to 122 GHz range. Alternatively, frequencies outside of this range, such as frequencies between 1 GHz and 20 GHz, or frequencies between 122 GHz, and 300 GHz, may also be used.

In some embodiments, the echo signals received by the receiving antennas of millimeter-wave radar 102 are filtered and amplified using band-pass filter (BPFs), low-pass filter (LPFs), mixers, low-noise amplifier (LNAs), and intermediate frequency (IF) amplifiers in ways known in the art. The echo signals are then digitized using one or more analog-to-digital converters (ADCs) for further processing. Other implementations are also possible.

Figure 2:
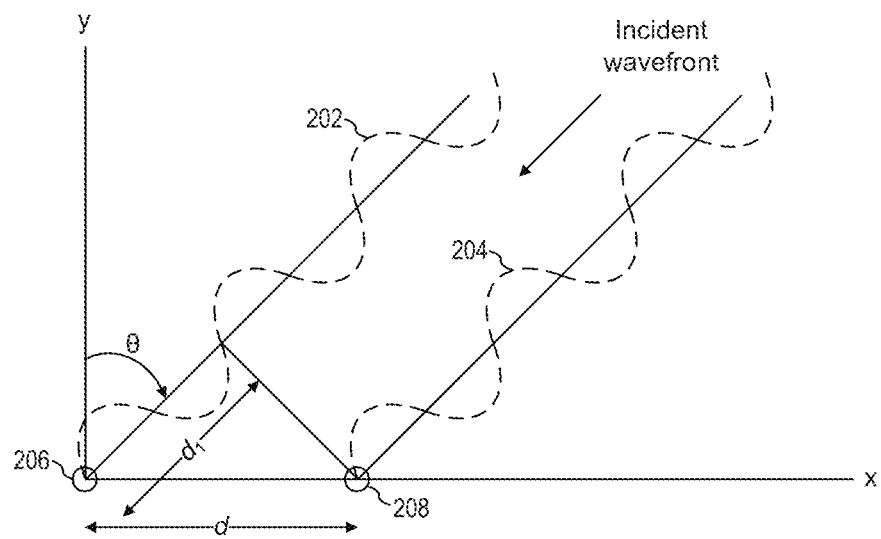
FIG. 2 illustrates an operation of an exemplary implementation of a phase mono-pulse technique for estimating the angle of arrival of incident signals.

Angle estimation for determining the azimuth component of the location of static or moving targets (e.g., humans) using a millimeter-wave radar may be performed using a phase mono-pulse algorithm. For example, FIG. 2 illustrates an operation of an exemplary implementation of a phase mono-pulse technique for estimating the angle of arrival of incident signals.

During normal operation, receiving antennas 206 and 208 of millimeter-wave radar 102, which are separated by a distance d, receive incident signals 202 and 204 after being reflected in objects in scene 108. Receiving antennas 206 and 208 receive incident signals 202 and 204 at different times based on the angle of arrival θ. For example, when incident signal 204 arrives at receiving antenna 208, incident signal 202 is at a distance $d_1$ from receiving antenna 206. Such phenomenon may be translated as a phase difference $\Delta\phi$, which may be given by $$\Delta\phi = \frac{2\pi}{\lambda} \cdot d \cdot \sin(\theta) \tag{1}$$

where λ is the wavelengths of incident signals 202 and 204, d is the distance between receiving antennas 206 and 208, and angle θ is the angle between incident signals 202 and 204 and a vertical axis y (also known as the angle of arrival). Therefore, angle of arrival θ may be estimated by $$\theta = \sin^{-1}\left(\frac{\Delta\phi\lambda}{2\pi d}\right) \qquad (2)$$

Figure 3:
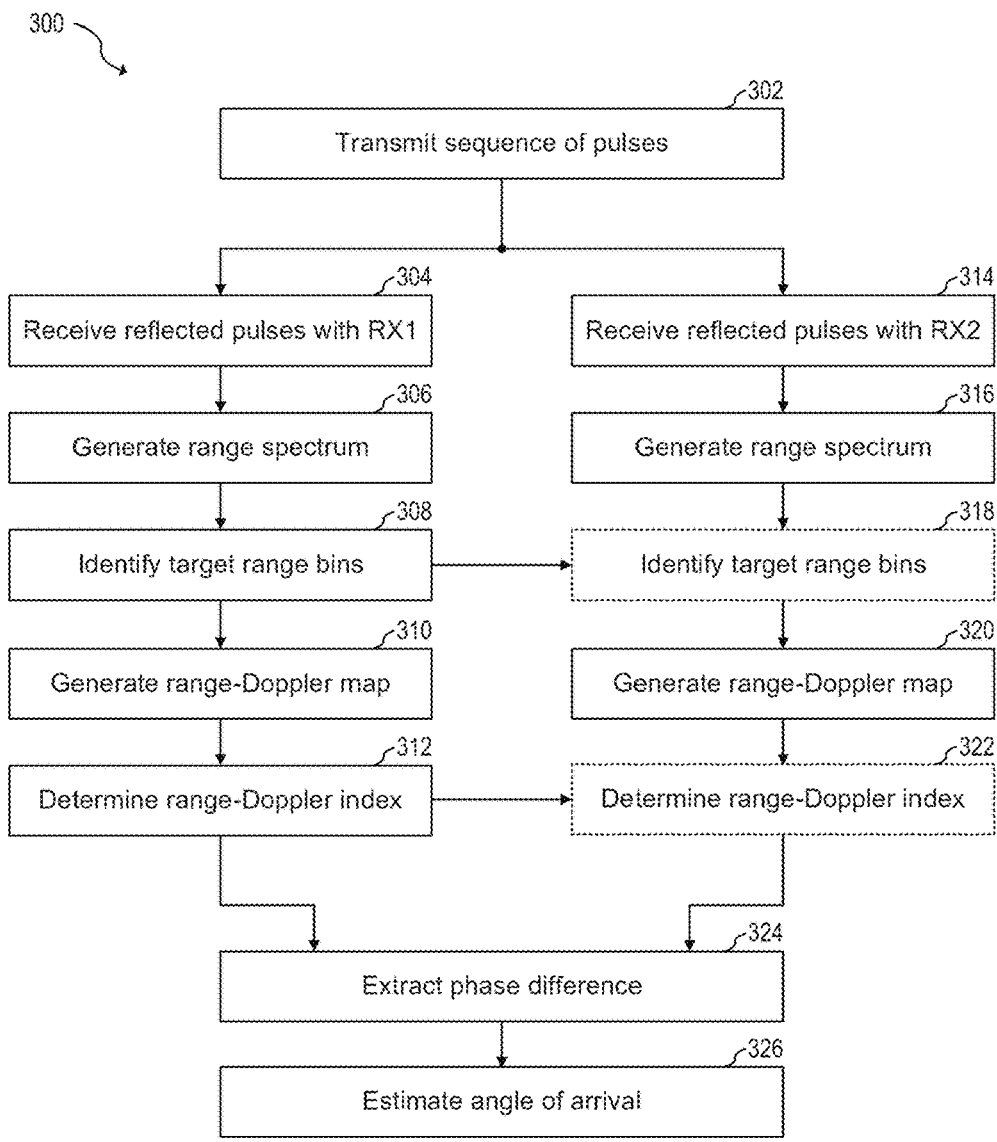
FIG. 3 illustrates a flow chart of an embodiment method of estimating the angle of arrival, according to an embodiment of the present invention.

FIG. 3 illustrates a flow chart of embodiment method 300 of estimating the angle of arrival, according to an embodiment of the present invention. Method 300 may be implemented, for example, by millimeter-wave radar 102.

During step 302, the millimeter-wave radar transmits a sequence of pulses, such as FMCW chirps, towards a scene, such as scene 108. The FMCW chirp signal $S_{TX}$ may be modelled as:

$$S_{TX}(t_f) = e^{j2\pi f_c t_f + \pi \beta t_f^2} \qquad (3)$$

where $f_c$ is the ramp/chirp start frequency, $T_c$ is the chirp time, $t_f$ represents the fast time within a chirp ($0 < t_f < T_c$), and β is the sweep bandwidth of the chirp, given by $$\beta = \frac{1}{T_c}.$$

A positive β represents an up-chirp and a negative β represents a down-chirp. The instantaneous frequency $f(t_f)$ may be given by $f(t_f) = f_c + \beta t_f$.

Receiver RX1 receives signal $S_{RX}$ using a respective receiving antenna, such as receiving antenna 206 during step 304. Similarly, receiver RX2 receives signal $S_{RX}$ using a respective receiving antenna, such as receiving antenna 208 during step 314. Signal $S_{RX}$ includes the reflected pulses.

An object in the field of view of the millimeter-wave radar located at base distance R may induce a round trip delay τ (between transmitted signal $S_{TX}$ and received signal $S_{RX}$) given by:

$$\tau(t_f) = \frac{2(R)}{c} \qquad (4)$$

where c is the speed of light. At the receiver (RX1 and RX2) an intermediate signal $S_{IF}$ may be generated by $S_{IF}(t_f) = S_{TX}(t_f) * S_{RX}(t_f)$ (e.g., de-ramping/de-chirping), which, after low-pass filtering may result in $$S_{IF}(t_f) = A \cdot e^{j(2\pi\beta\tau(t_f)t_f - \pi\beta\tau(t_f)^2 + 2\pi f_c \tau(t_f))} \qquad (5)$$

where A is a factor that captures the path loss attenuation, antenna gains, receiver gains, and target radar cross-section (RCS).

During step 306, range spectra are generated, e.g., using an FFT, in fast time, based on the reflected pulses received by receiver RX1 (e.g., using intermediate frequency signal $S_{IF}$). For example, in some embodiments, each received pulse is processed to generate a corresponding intermediate signal pulse, and an FFT is performed on each corresponding intermediate signal pulse to generate a corresponding spectrum. Terms that are independent of time $t_f$ appear as a phase offset in the frequency domain. An FFT along the fast time of the intermediate frequency signal $S_{IF}$ (for each pulse), therefore, may result in an observable peak at $$f_{IF} = \beta\tau(t_f) = \frac{\beta 2R}{c}$$

(ignoring a velocity v of the target), where each bin of each range spectrum of the generated range spectra represents a distance from the millimeter-wave radar. Such peak may be associated with a target (i.e., a target present in the range R associated with the bin in which the peak is present).

During step 316, range spectra are generated, in fast time, based on the reflected pulses received by receiver RX2 in a similar manner as in step 306.

During step 308, range bins of the spectrum generated during step 306 are associated with targets (e.g., humans). In some embodiments, targets are identified during step 308 using a peak searching algorithm that compares the value of each bin with a threshold. In some embodiments, for bins containing values greater than the threshold, a peak $f_p$ is identified by scanning the range bin vector from, e.g., left to right, and by detecting a negative slope from adjacent bins. For example, if a $bin_0$ contains a value less than or equal to the value of the $bin_{-1}$ immediately to the left and $bin_{-2}$ immediately to the left of $bin_{-1}$, or if $bin_0$ contains a value that is greater than the value of $bin_{+1}$ immediately to the right and $bin_{+2}$ immediately to the right of $bin_{+1}$, a peak $f_p$ is identified in $bin_0$.

In some embodiments, range bins adjacent to the bin exhibiting a peak are also associated with a target to account for possible errors in the range bin identification (e.g., one bin before and one bin after the range bin exhibiting the peak, two bins before and two bins after the range bin exhibiting the peak, etc.). In some embodiments, therefore, a set of bins is used as an initial coarse estimate for range detection. In some embodiments, multiple targets are identified. Method 300 may also apply to multiple targets.

In some embodiments, range bins of the spectrum generated during step 316 are associated with targets (e.g., humans) during step 318. However, since the target range bins identified during step 308 are typically equal to the target range bins identified during step 318, some embodiments skip step 318.

During step 310, a range-Doppler map is generated using a Doppler FFT on the identified target range bins (step 308) of the range spectrum generated during step 306. A range-Doppler map is generated by performing an FFT, in slow time, for the range bins associated with the target in step 308. The range-Doppler map results in a map having an axis (e.g., the x axis) associated with range R, and an axis (e.g., the y axis) associated with Doppler velocity v. A peak at an index $(x_i, y_j)$ of the range-Doppler map is associated with a target present at range $R_i$ and traveling with Doppler velocity $v_j$, where range $R_i$ corresponds with bin i of the range bins, and Doppler velocity $v_j$ corresponds with bin j of the Doppler velocity bins. During step 320 a range-Doppler map is generated using a Doppler FFT on the identified target range bins (step 308 or 318) of the range spectrum generated during step 316. By performing a range-Doppler FFT on a limited set of ranges, computational time and power is advantageously reduced without sacrificing accuracy.

During step 312, a range-Doppler index is identified for each target based on the range-Doppler map generated during step 310. In some embodiments, the range-Doppler indices are identified using a two-dimensional (2D) peak search algorithm. In some embodiments, a range-Doppler index is identified during step 322 for each target based on the range-Doppler map generated during step 320. However, since range-Doppler indices identified during step 312 are typically equal to range-Doppler indices identified during step 322, some embodiments may skip step 322.

During step 324, a phase difference between signals received by receivers RX1 and RX2 is determined for each identified target based on the range-Doppler maps (generated during steps 310 and 320) using the range-Doppler indices determined during steps 312 (and 322). For example, in some embodiments, the phase difference is extracted by calculating the phase of the received RX1 and RX2 signals by taking the arc tangent along the I (in-phase) and Q (quadrature) channels based on the determined range-Doppler index, such as given by $$\Delta\phi = \arctan\left(\frac{Q_{RX1}}{I_{RX1}}\right) - \arctan\left(\frac{Q_{RX2}}{I_{RX2}}\right) \quad (6)$$

where the phase $\phi_{RX1}$ corresponding to the received signal RX1 is given by $$\phi_{RX1} = \arctan\left(\frac{Q_{RX1}}{I_{RX1}}\right),$$

and the phase $\phi_{RX2}$ corresponding to the received signal RX2 is given by $$\phi_{RX2} = \arctan\left(\frac{Q_{RX2}}{I_{RX2}}\right).$$

During step 326, the angle of arrival is estimated using a phase mono-pulse algorithm, such as by using Equation 2. In some embodiments, the estimated angle of arrival is stored for further processing (e.g., for target location predictions or to improve the accuracy of future angle of arrival estimates).

As illustrated by Equation 2, the accuracy of the estimated angle θ (determined in step 326) depends on the accuracy of the phase difference Δϕ. The phase difference Δϕ may be affected, for example, by Doppler components of the target. For example, when M pulses are transmitted towards a static object, phase and amplitude of each of the corresponding M reflected pulses are substantially identical to each other. When the target object is moving (e.g., a moving human), the phase information of each of the M reflected pulses varies depending on the direction of movement, velocity, etc. For example, in the presence of a target that generates a Doppler frequency $f_d$, the received signal $S_{RX}$ may be given by $$S_{RX}(t_f) = e^{j2\pi(f_c + f_d)(t_f - \tau(t_f)) + \pi\beta(t_f - \tau(t_f))^2} \quad (7)$$

where $$f_d = \frac{2vf_c}{c},$$

and v is the velocity in which the target is moving away from the millimeter-wave radar or approaching the millimeter-wave radar.

The Doppler frequency $f_d$ may result in a change in amplitude and phase of intermediate frequency signal $S_{IF}$ over slow time. Thus, it is possible to estimate the velocity v by performing an FFT along the slow time and comparing the peaks of the FFT with a threshold, where the estimated velocity corresponds to the bin in which the peak is detected. For example, a data vector $Y(t_s)$ of the received ADC data after mixing at the receiver (e.g., $S_{IF}$ corresponding to the RX1 receiver) for a range bin associated with the $k_{th}$ target along slow time, after applying an FFT, may be given by:

$$Y(t_s) = [\rho_k \rho_k e^{jw_k T_{PRT}} \ldots \rho_k e^{j(N_P - 1)w_k T_{PRT}}] \quad (8)$$

where $t_s$ represents the slow time across chirps in a frame, $\rho_k$ is a constant, $T_{PRT}$ is the pulse repetition time (i.e., the time between two consecutive chirps), $N_P$ is the number of chirps in the frame, and $w_k$ is the twiddle factor $$\left(w_k = \frac{2\pi}{N_P}\right).$$

In some embodiments, $T_{PRT}$ is equal to 500 μs, and $N_P$ is equal to 16 or 32.

In an embodiment of the present invention, the macro-Doppler components associated with a moving human are estimated and subtracted from the range-Doppler map (steps 310 and 320) before extracting the phase difference (in step 324), thus compensating for effects of Doppler components in the estimation of angle of arrival θ, thereby increasing the angle of arrival θ accuracy. In some embodiments, the macro-Doppler components associated with a moving human are subtracted from the range-Doppler map by extracting the peak from the I+jQ data from the range-Doppler map.

Figure 4:
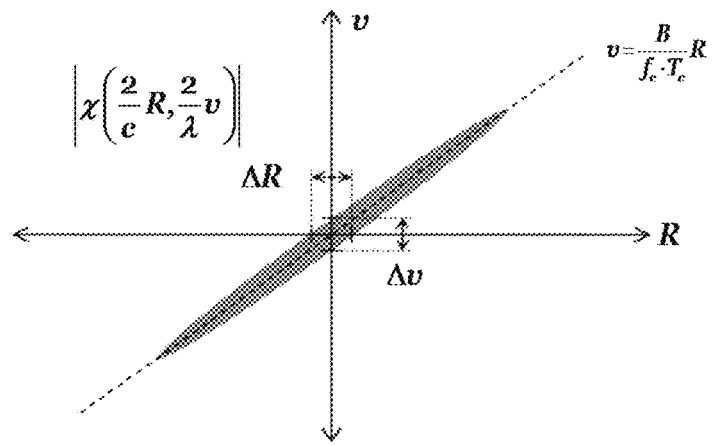
FIG. 4 shows an ambiguity function of a conventional FMCW waveform.

Doppler components of the target may also affect range estimations (step 308). For example, FIG. 4 shows ambiguity function χ of a conventional FMCW waveform. As shown in FIG. 4, when target Doppler velocity v is zero, the error contribution of the Doppler components associated with the Doppler velocity v to range R is zero. However, when the target Doppler velocity v is not zero (either positive or negative Doppler velocity v), there is a corresponding error ΔR associated with range R. Since the ambiguity function χ is known for a particular system, it is possible to perform the identification of target range bins (step 308) taking into account the ambiguity function and the typical movement velocity v of a human. For example, in some embodiments, the range uncertainty determined based on the ambiguity function χ is ±2 range bins. In such a system, when a peak is identified in, e.g., range bin 25 during step 308, range bins 23-27 are also considered when generating the range-Doppler map during step 310 (and 320). By identifying the range uncertainty based on the ambiguity function, errors in range identification are minimized without excessively increasing the amount of computations performed.

Method 300 is sensitive to SNR. For example, low SNR in the range spectrum generated in step 306 may result in failure to identify a target. In an embodiment of the present invention, SNR is improved by performing coherent integration of N received pulses (e.g., during step 306), where N is the total number of chirps in a frame. For example, in an embodiment, an ADC is used to sample the signal received by a receiver (e.g., in step 304). An FFT is performed on each pulse received in fast time (e.g., in step 306). N FFTs of consecutive pulses are added up coherently (i.e., range bin by range bin) before, e.g., step 308. The coherently integrated FFT has higher SNR than each individual FFT because uncorrelated noise of each individual FFT tends to cancel out when integrated while correlated information (e.g., the peak representing the range of the target) does not. In some embodiments, N is equal to 16 or 32. Other number of pulses for coherent integration may also be used.

Figure 5:
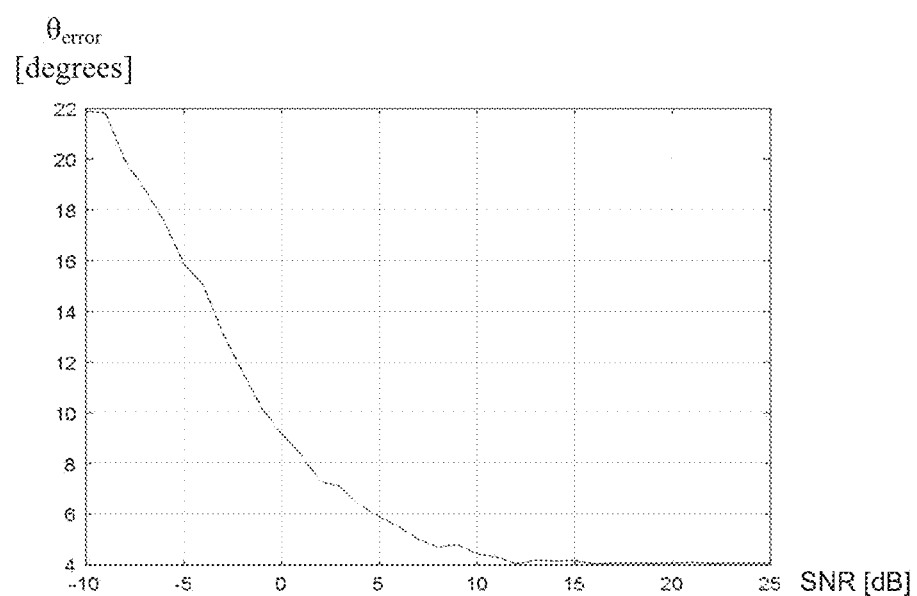
FIG. 5 shows a graph of angle estimation error using a phase mono-pulse technique versus signal-to-noise ratio (SNR)

As another example, low SNR in the range-Doppler map may result in an error in the estimated angle of arrival θ. For example, FIG. 5 shows a graph of angle estimation error using a phase mono-pulse technique versus SNR of the range-Doppler map after Doppler velocity compensation. Performing angle estimation with low SNR may also result in the angle estimation at the edges of the filed-of-view (FoV) of the millimeter-wave radar to jump from one side to the other side of the FoV, meaning that the target may be estimated to be, e.g., at 25°, when the target is actually at −25°.

To avoid erroneous estimation of angle of arrival θ, some embodiments estimate the angle of arrival θ (step 326) based on the range-Doppler maps generated in steps 310 and 320 only if the SNR of the range-Doppler maps are above an SNR threshold (e.g., higher than 10 dB). In some embodiments, the SNR threshold is based on the range threshold used to identify peaks during step 308. For example, in an embodiment, the range threshold for peak identification during step 306 is $th_1$, and the SNR threshold for determining whether to estimate angle of arrival θ is $1.2*th_1$.

Figure 6:
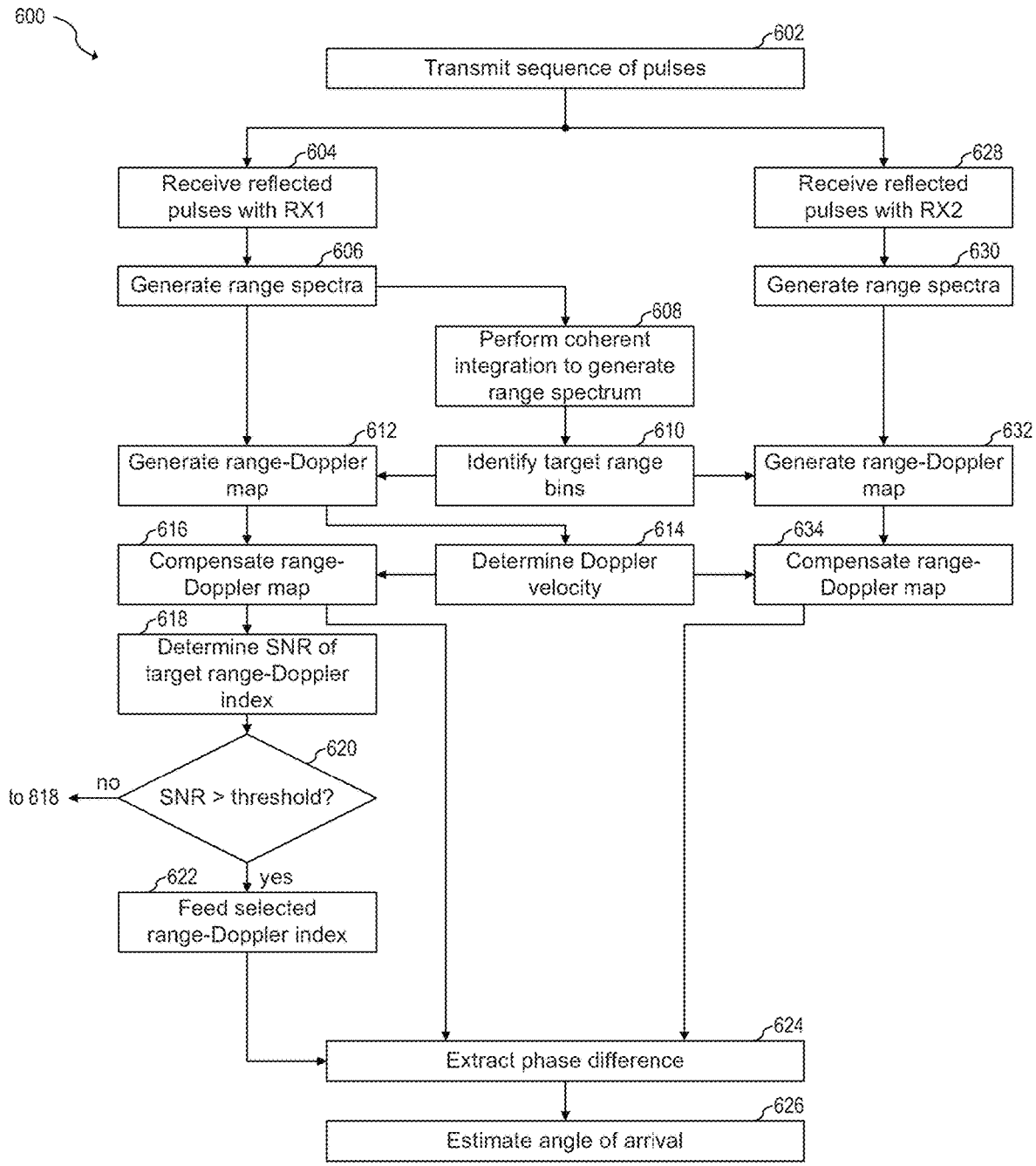
FIGS. 6-8 illustrate flow charts of embodiment methods of estimating the angle of arrival, according to embodiments of the present invention.

FIG. 6 illustrates a flow chart of embodiment method 600 of estimating the angle of arrival, according to an embodiment of the present invention. Method 600 may be implemented, for example, by millimeter-wave radar 102.

During step 602, the millimeter-wave radar transmits a sequence of pulses in a similar manner as in step 302. During step 604 and 628, receivers RX1 and RX2 receive reflected pulses in a similar manner as in steps 304 and 314, respectively. Some embodiments use more than two antennas for determining angle of arrival.

During steps 606 and 630, range spectra are generated on a frame of pulses received by receiver RX1 and RX2 in a similar manner as in steps 306 and 316, respectively. During step 608, coherent integration of the range spectra of the frame is performed to generate an integrated spectrum. During step 610, range bins of the integrated range spectrum are associated with targets in a similar manner as in step 308. In some embodiments, the range bins are identified taking into account range uncertainty (e.g., based on the ambiguity function). In some embodiments, it is possible to identify multiple targets.

During steps 612 and 632, range-Doppler maps are respectively generated based on respective range spectra (generated in steps 606 and 630) using the targets identified in step 610. During step 614, the Doppler velocity of each identified target is determined based on the range-Doppler map generated in step 612 (and/or in step 632).

During step 616, the range-Doppler map (e.g., generated in step 612) is compensated for the corresponding Doppler velocity of each identified target. The range-Doppler map is compensated by selecting target range-Doppler peaks. For example, if a target has velocity $v_T=k \cdot 1/PRT$, where PRT is the pulse repetition time, the phase difference induced along slow-time is $\phi_s = e^{-j \cdot 2 \cdot \pi \cdot n \cdot 1/PRT}$. In other words, taking the FFT along the slow time, the $k^{th}$ Doppler bin has the peak of the signal, which represents the Doppler of the target. Thus, once the peak is selected, the range-Doppler map is, in effect, compensated for the Doppler component of the identified target. Similarly, during step 634, the range-Doppler map (e.g., generated in step 632) is compensated for the corresponding Doppler velocity of each identified target.

The SNR for each target range-Doppler index (e.g., from step 616) is determined in step 618. If it is determined during step 620 that the SNR of a target range-Doppler index is sufficiently high (e.g., higher than 1.2 times the range threshold), such target range-Doppler index is used to extract phase difference during step 624. If it is determined that the SNR is low (e.g., lower than 1.2 times the range threshold), then, in some embodiments, the associated phase information is discarded and not used for estimating the angle of arrival, e.g., as described with respect to step 818.

During step 624, a phase difference between signals received by receivers RX1 and RX2 is determined for each identified target in a similar manner as in step 324. During step 626, the angle of arrival is determined in a similar manner as in step 326.

When static human targets are present, micro-Doppler components associated with vital signs of the static human target (e.g., breathing) may cause a phase rotation of the signal at the range where the static human target is present, thereby affecting the accuracy of the estimated angle θ. For example, the respiratory rate of a static human may range from 12 to 20 breaths per minute (0.2 Hz-0.4 Hz) and may have an associated displacement of the chest wall of up to around 7.5 mm.

In an embodiment of the present invention, the phase rotation associated with Doppler components generated by vitals of the target human (e.g., breathing) is compensated by aggregating the mean Doppler FFT data on the identified target range over a time sufficient to capture the frequency of the vital (e.g., 3.2 seconds for breathing). The vital frequency is estimated by performing a peak search on the generated Doppler FFT. The bin showing the vital frequency is used to determine the angle of arrival based on the signals received by receivers RX1 and RX2.

Figure 7:
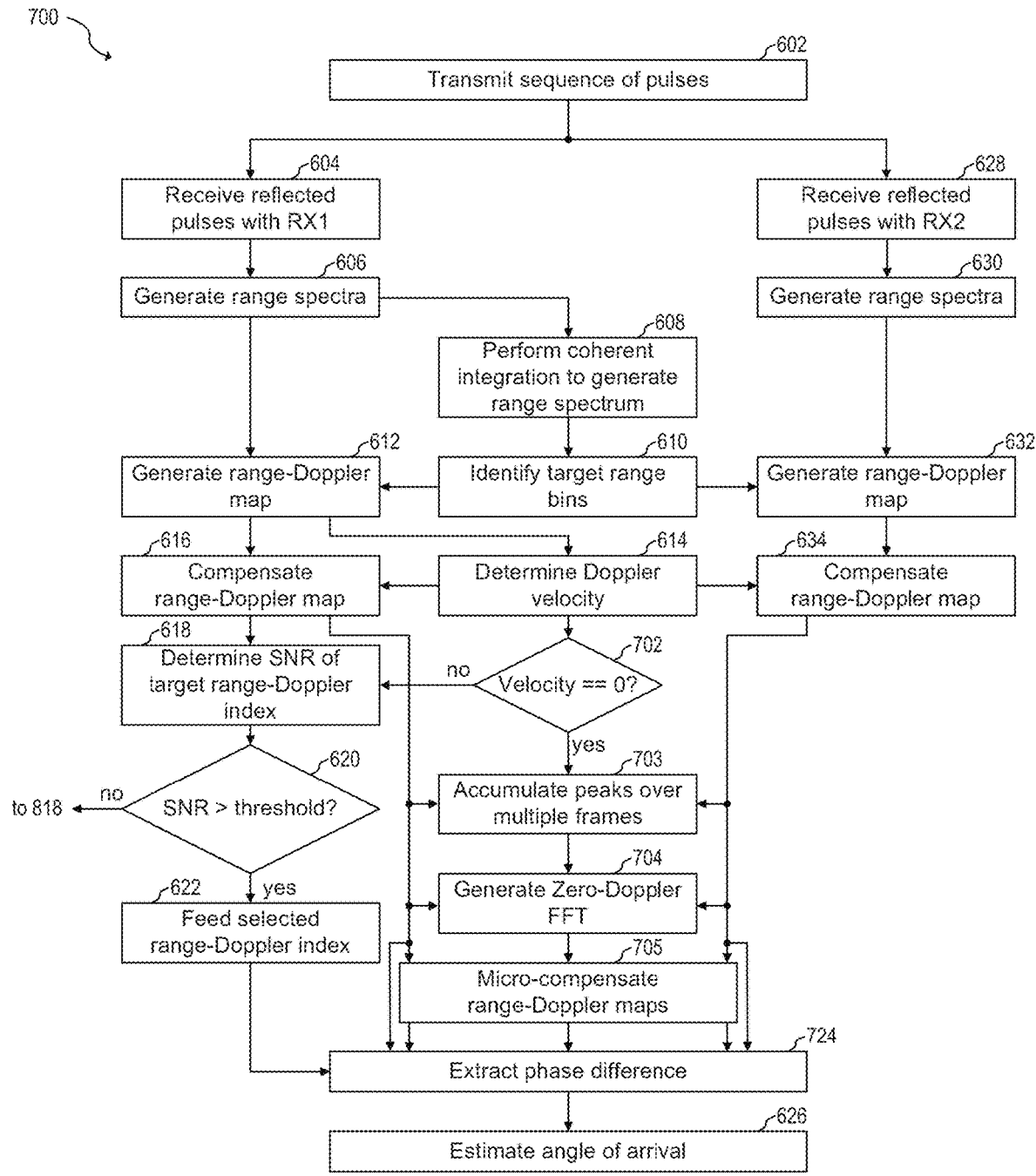

FIG. 7 illustrates a flow chart of embodiment method 700 of estimating the angle of arrival, according to an embodiment of the present invention. Method 700 may operate in a similar manner as method 600. Method 700, however, also compensate for Doppler components associated with vital signals of a static human. For example, during step 702, it is determined whether the target human is static or moving. If the target human is moving, method 700 proceeds in a similar manner as method 600.

If the target human is determined to be static, then the zero-Doppler peak values of the compensated range-Doppler map are captured over a plurality of frames (step 703) in respective vectors (one per receiver) and an FFT of the vector is computed during step 704. For example, in some embodiments, an array is used to accumulate peaks over multiple frames during step 703. The zero-Doppler FFT vector is used to compensate the range-Doppler maps from steps 616 and 634 for micro-Doppler components, such as breathing, hand movements, etc., during step 705. In some embodiments, the respective zero-Doppler vectors are based on the range-Doppler maps generated in steps 612 and 632 without compensating them in steps 616 and 634. Performing steps 703, 704, and 705 advantageously allows for compensating for low frequency Doppler velocities (e.g., lower than 1 Hz).

As a non-limiting example, in an embodiment in which each frame takes 200 μs, 16 frames may be used during step 704, resulting in the utilization of 3.2 seconds of data. Different number of frames and frames with a different duration may be used.

During step 724, when the humans are moving, the phase difference is determined in a similar manner as in step 624. If the humans are static, however, the phase difference is based in the micro-Doppler compensated range-Doppler maps from step 705 (one for each receiver) instead of the compensated range-Doppler maps from steps 616 and 634. The angle of arrival is estimated in step 626 based on the phase difference determined in step 724.

Figure 8:
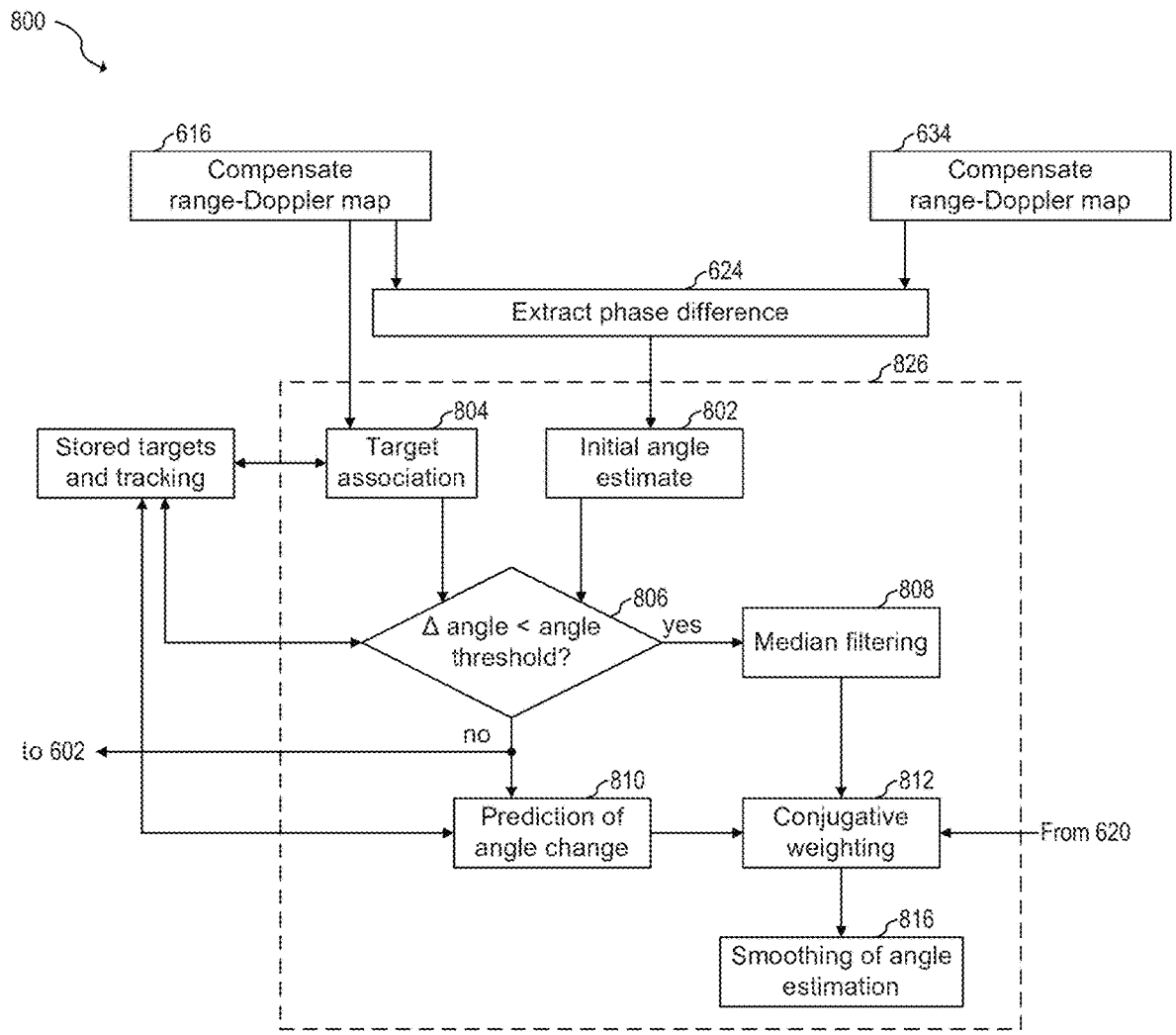

In some embodiments, methods 300, 600 and 700 are performed continuously. In some embodiments, target tracking and angle tracking is performed to improve the accuracy of the estimated angle of arrival. For example, FIG. 8 illustrates a flow chart of embodiment method 800 of estimating the angle of arrival, according to an embodiment of the present invention. The discussion that follows assumes that method 800 is implemented as part of method 600 (some steps have been omitted for clarity purposes). However, method 800 may be implemented with other methods of estimating the angle of arrival, such as methods 300, or 700, for example.

During step 826, the angle of arrival is determined. Step 826 includes steps 802, 804, 806, 808, 810, 812, and 816. In some embodiments, one or more of steps 806, 808, 810, 812, and 816 are skipped.

During step 802, an initial angle of arrival is estimated using the phase mono-pulse algorithm based on the phase difference extracted in step 624 for each identified target.

During step 804, each identified target is associated with a tracked target (e.g., previously stored in memory) based on the range and Doppler velocity (estimated in step 616). For example, during step 804, the range and Doppler velocity of each identified target may be compared with historic tracks of previously identified targets (e.g., stored in memory). Each identified target, then, may be associated with a track in which the last reported range and Doppler velocity are closest to it.

If no track has a range and Doppler velocity that are close enough to a particular identified track, then, in some embodiments, a new track is created. In some embodiments, correlation between variations of identified targets are performed to determine if the identified target is a ghost human (e.g., a target suddenly appears in a location that would have required a human to move faster than humanly possible). If a target is identified as a ghost human, then no track is associated with such identified target. In some embodiments, static humans are not tracked (only tracked when the human moves).

Tracks that are not associated with an identified target (e.g., because the last range and/or Doppler velocity may not be associated with a human moving into currently identified range or Doppler velocity), may be cancelled. Other tracking methods may be used.

The difference in angle of arrival estimated in step 802 and the previous angle of arrival (e.g., based on stored data) is determined during step 806. If the difference is greater that a threshold (which may be determined, for example, based on the velocity of a typical moving human), the angle of arrival is not updated. For example, in some embodiments, if the difference is greater that a threshold, the angle of arrival determined during step 802 is not used for tracking purposes, and not used for reporting the angle of arrival during step 826. For example, some embodiments may use a predicted angle of arrival (e.g., generated during step 810) instead of the estimated angle of arrival (estimated during step 802) for tracking purposes (e.g., storing in memory) and as an output of step 826.

If the angle of arrival is lower than the threshold, a sequence of Q angles of arrivals (where Q includes Q−1 previously stored angles of arrival and the currently estimated angle of arrival) is filtered using a median filter to remove outliers during step 808.

During step 810, a prediction of angle of arrival change for each identified target is generated based on an estimate of tangential velocity of each identified target (e.g., based on previously stored range and angle of arrival for the respective identified target).

Weighting between the predicted angle of arrival and the estimated angle of arrival (after filtering in step 808) is performed during step 812. For example, if an identified target has an SNR higher than an SNR threshold (see step 620) and the difference in angle of arrival estimated in step 802 and the previous angle of arrival is lower than an angle threshold (see step 806), then the weights used for the predicted angle (step 810) and the measured angled (802, 808) may be 0.5 for each. If the identified target has an SNR lower than the SNR threshold (see step 620) or the difference in angle of arrival estimated in step 802 and the previous angle of arrival is higher than the angle threshold (see step 806), then the weights used for the predicted angle (step 810) and the measured angled (802, 808) may be 1 and 0, respective (in other words, no weight is assigned to the estimated angle of arrival and 100% weight is assigned to the predicted angle of arrival.

In some embodiments, the weights applied to the predicted angle of arrival and the estimated angle of arrival may be predetermined. In other embodiments, the weights applied to the predicted angle of arrival and the estimated angle of arrival are dynamically generated using, e.g., a Kalman filter or Bayesian techniques, or according to a predetermined rule(s).

During step 816, the angle of arrival is smoothened using a moving average. For example, in some embodiments, the estimated angle of arrival $\theta_i^m$ is smoothened in step 816, for example, by $$\theta_i^m = \alpha \cdot \theta_{i-1} + (\alpha-1) \cdot \theta_{i-1}^m \qquad (9)$$

where $\alpha$ is a number between 0 and 1 (e.g., 0.5), $\theta_i^m$ is the smoothened angle of arrival, $\theta_{i-1}^m$ is the previous smoothened angle of arrival, and $\theta_{i-1}^m$ is the current estimated angle of arrival (after steps 808 and 812).

Advantages of some embodiments include the capability of accurately estimating angle of arrival of radar signals reflected in moving or static humans in low SNR regimes. Additional advantages include the improvement of SNR of reflected radar signals, thereby improving the estimate of angle of arrival. By improving the SNR, the update rate (i.e., the times in which the angle of arrival is updated—see step 620, for example) is increased. In some embodiments, by improving the estimation of the angle of arrival and by increasing the rate in which the angle of arrival is estimated, the estimation of the location of a human (including the azimuth component), and the tracking of the human in space are also improved.

Some embodiments, such as methods 300, 600, 700 and 800, may be used in various applications FIGS. 9-12 show non-limiting examples of applications of methods 300, 600, 700, and 800.

Figure 9:
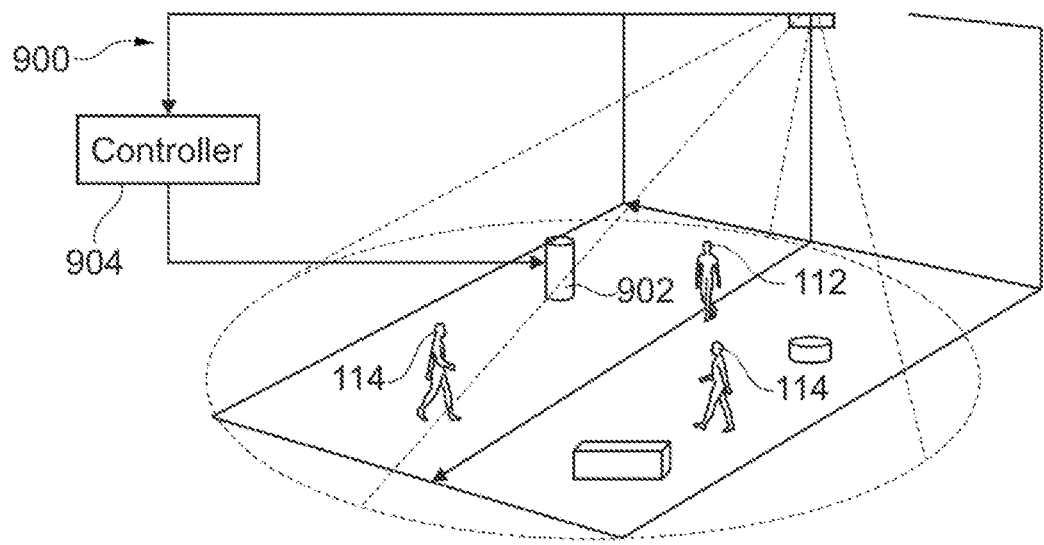
FIGS. 9-12 show non-limiting examples of applications of the embodiment methods of FIGS. 3 and 6-8, according to embodiments of the present invention.

FIG. 9 shows room 900 having sound system 902, according to an embodiment of the present invention. During normal operation, millimeter-wave radar 102 estimates the azimuth component of humans by estimating the angle of arrival using, e.g., method 300, 600, 700, or 800. Controller 904 receives (e.g., wirelessly) the azimuth components of moving (114) or static (112) humans and causes sound system 902 to direct sound to the direction of humans (e.g., using beamforming techniques known in the art).

Figure 10:
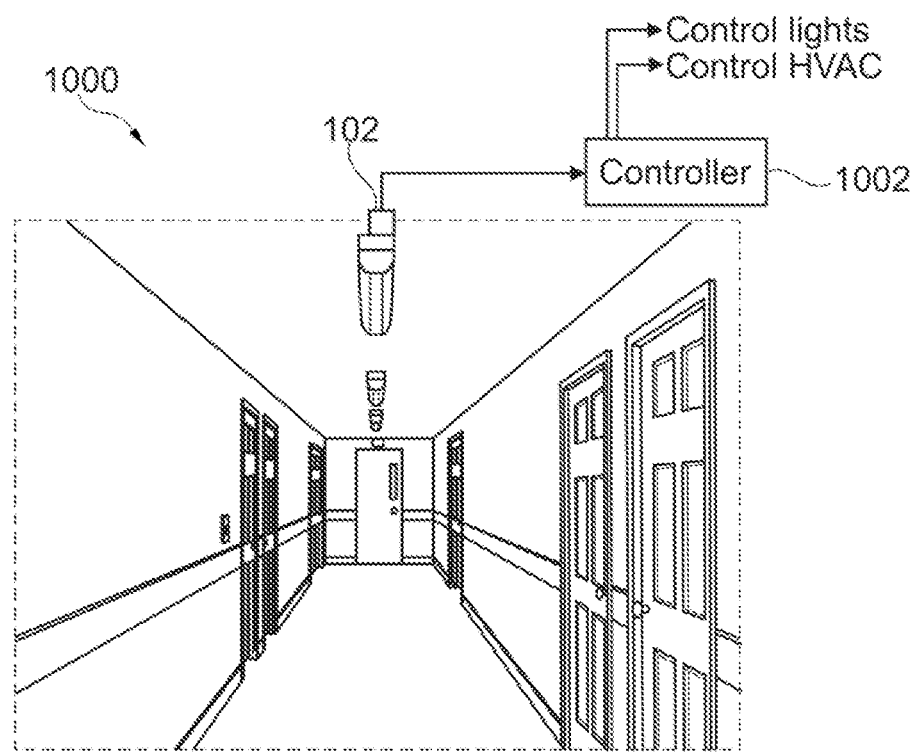

FIG. 10 shows hotel hallway 1000, according to an embodiment of the present invention. During normal operation, millimeter-wave radar 102 (which may be installed in a ceiling of hotel hallway 1000, for example) controls one or more hotel room functions based on tracking the angle of arrival of humans moving in hotel hallway 1000. For example, in some embodiments, millimeter-wave radar 102 determines whether humans are inside each hotel room based on estimating and tracking the angle of arrival of humans as they move through hotel hallway 1000. Based on the detected human movement, millimeter-wave-radar 102 determines if humans have entered or exited each hotel room, and counts the number of humans entering or exiting each hotel room. Controller 1002 controls lights and/or HVAC of each hotel room based on the number of humans in each hotel room (e.g., controller 1002 turns off lights and HVAC in a hotel room having no humans).

Figure 11:
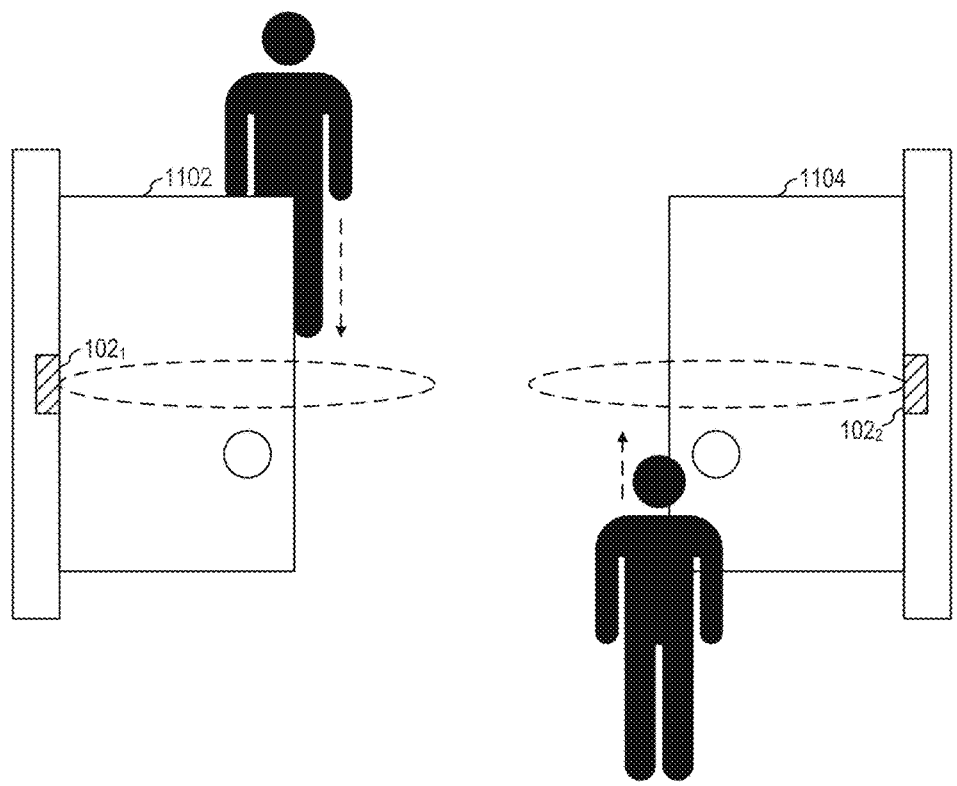
Figure 12:
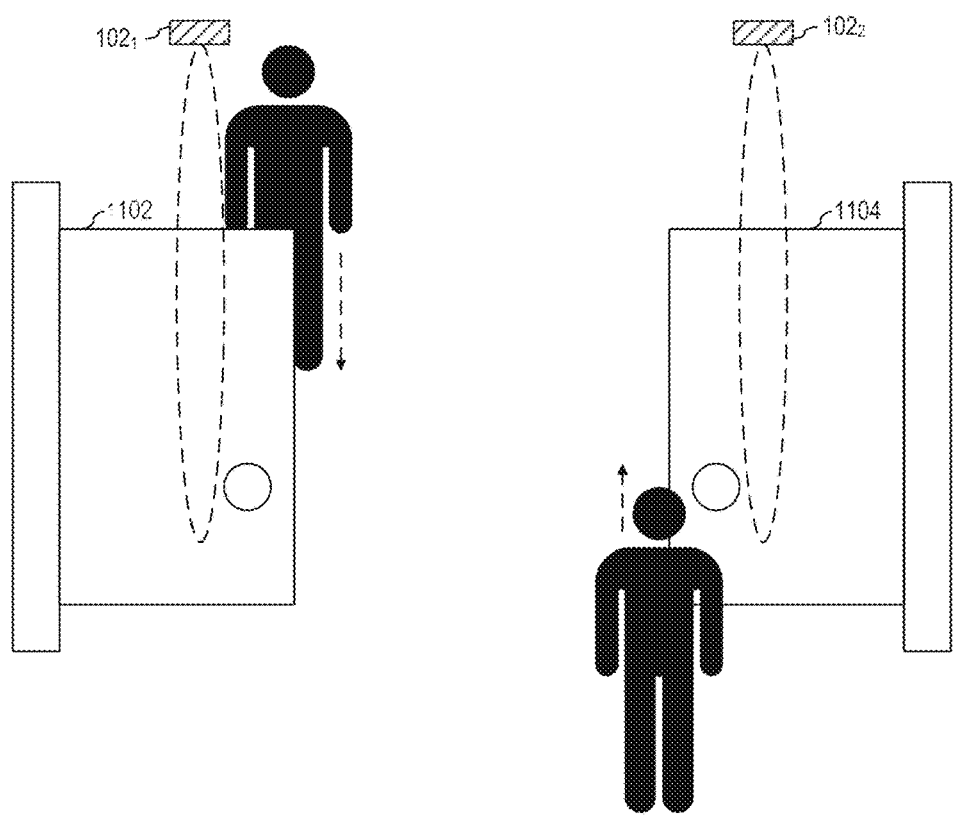

FIG. 11 shows automatic gates 1102 and 1104, according to an embodiment of the present invention. Automatic doors 1102 and 1104 include respective millimeter-wave radars $102_1$ and $102_2$. During normal operation, millimeter-wave radars $102_1$ and $102_2$ causes automatic doors 1102 and 1104 to open or close based on humans movement. Millimeter-wave radars $102_1$ and $102_2$ also count the number of humans crossing in each direction by tracking the angle of arrival of human targets as they move through respective fields-of view 1106 and 1108 of millimeter-wave radars 1102 and 1104. As shown in FIG. 11, millimeter-wave radars 102, and $102_2$ are installed in automatic gates 1102 and 1104 and have the capability of detecting angle of arrival in a horizontal direction (i.e., parallel to the floor). FIG. 12 shows another embodiment that operates in a similar manner as the embodiment of FIG. 11. The embodiment of FIG. 12, however, has millimeter-wave radars $102_1$ and $102_2$ installed at a ceiling and having the capability of detecting angle of arrival in a vertical direction (i.e., perpendicular to the floor).

Example embodiments of the present invention are summarized here. Other embodiments can also be understood from the entirety of the specification and the claims filed herein.

Example 1

A method of estimating an angle of arrival of a radar signal reflected on a human target, the method including: receiving the reflected radar signal with first and second antennas of a millimeter-wave radar; transforming the reflected radar signal received with the first and second antennas to generate first and second range spectrum, respectively; generating a first range-Doppler map based on the first range spectrum; generating a second range-Doppler map based on the second range spectrum; determining or estimating a Doppler velocity based on the first range-Doppler map or the second range-Doppler map; macro-compensating the first range-Doppler map and the second range-Doppler map by selecting a peak in the first range-Doppler map or the second range-Doppler map based on the determined Doppler velocity; identifying an index of the first macro-compensated range-Doppler map corresponding to an identified target; estimating a phase difference based on the first and second macro-compensated range-Doppler maps and the identified index; and estimating the angle of arrival based on the phase difference.

Example 2

The method of example 1, further including identifying a set of target range bins based on the first range spectrum, where generating the first range-Doppler map is further based on the set of target range bins.

Example 3

The method of one of examples 1 or 2, where identifying the set of target range bins is based on an ambiguity function associated with a transmitted radar signal.

Example 4

The method of one of examples 1 to 3, where the set of target range bins includes a plurality of consecutive range bins.

Example 5

The method of one of examples 1 to 4, where identifying the set of target range bins includes performing a peak search on the first range spectrum to generated an identified target range bin.

Example 6

The method of one of examples 1 to 5, where the set of target range bins includes at least three range bins, where the three range bins are centered at the identified target range bin.

Example 7

The method of one of examples 1 to 6, where generating the first range spectrum includes: performing N Fourier transforms on N respective pulses of the reflected radar signal received with the first antenna to generate N range spectra, N being a positive integer greater than 1; and coherently integrating the N range spectra to generate the first range spectrum.

Example 8

The method of one of examples 1 to 7, where N is equal to 16 or 32.

Example 9

The method of one of examples 1 to 8, where N corresponds to a total number of pulses within a frame.

Example 10

The method of one of examples 1 to 9, further including: generating a zero-Doppler array based on first or second macro-compensated range-Doppler maps; determining a vital frequency of a vital sign of a human by selecting a peak of the zero-Doppler array; and micro-compensating the first and second range-Doppler maps or the first and second macro-compensated range-Doppler maps based on the vital frequency.

Example 11

The method of one of examples 1 to 10, where determining the vital frequency includes performing a Fourier transform in slow time based on the first range-Doppler map.

Example 12

The method of one of examples 1 to 11, where the vital sign corresponds to breathing of a human, and where the vital frequency corresponds to a breathing frequency of a human.

Example 13

The method of one of examples 1 to 12, where determining the vital frequency includes accumulating zero-Doppler peak values of the first macro-compensated range-Doppler map over a plurality of frames.

Example 14

The method of one of examples 1 to 13, where the vital frequency has a frequency lower than 1 Hz.

Example 15

The method of one of examples 1 to 14, further including determining a signal-to-noise ratio (SNR) of the identified target in the first range-Doppler map, where estimating the angle of arrival includes updating the angle of arrival associated with the identified only when the SNR is higher than an SNR threshold.

Example 16

The method of one of examples 1 to 15, further including identifying a target range bin by comparing bin values of the first range spectrum with a range threshold, where generating the first range-Doppler map is based on the target range bin, and where the SNR threshold is based on a range threshold.

Example 17

The method of one of examples 1 to 16, where the SNR threshold is substantially equal to 1.2 times the range threshold.

Example 18

The method of one of examples 1 to 17, further including transmitting a radar signal towards the human target using the millimeter-wave radar, the transmitted radar signal including a sequence of pulses.

Example 19

The method of one of examples 1 to 18, where each pulse of the sequence of pulses is a linear chirp.

Example 20

The method of one of examples 1 to 19, where identifying the index of the first macro-compensated range-Doppler map includes performing a two-dimensional peak search of the macro-compensated first range-Doppler map.

Example 21

The method of one of examples 1 to 20, further including: estimating an initial second angle of arrival; comparing the angle of arrival with the initial second angle of arrival to generate a first difference; and when a magnitude of the first difference is higher than an angle threshold, predicting a second angle of arrival based on the angle of arrival and generating a second angle of arrival based on a predicted second angle of arrival, or avoid generating the second angle of arrival.

Example 22

The method of one of examples 1 to 21, further including: when the magnitude of the first difference is lower than the angle threshold, filtering the initial second angle of arrival to generate a filtered second angle of arrival with a median filter; and generating the second angle of arrival based on the filtered second angle of arrival.

Example 23

The method of one of examples 1 to 22, further including: when the magnitude of the first difference is lower than the angle threshold, performing conjugative weighting between the predicted second angle of arrival and a value of an angle of arrival based on the initial second angle of arrival to generate a weighted second angle of arrival; and generating the second angle of arrival based on the weighted second angle of arrival.

Example 24

The method of one of examples 1 to 23, further including: when the magnitude of the first difference is lower than the angle threshold, smoothening a value of an angle of arrival based on the initial second angle of arrival to generate a smoothened second angle of arrival; and generating the second angle of arrival based on the smoothened second angle of arrival.

Example 25

The method of one of examples 1 to 24, further including: storing location data of an identified target in a memory based on the estimated angle of arrival; and tracking the location data of the identified target over time, where estimating the angle of arrival is further based on the tracked location data.

Example 26

The method of one of examples 1 to 25, further including: estimating an initial second angle of arrival; and associating the initial second angle of arrival with a track.

Example 27

The method of one of examples 1 to 26, further including determining if the initial second angle of arrival corresponds to a ghost human, where associating the initial second angle of arrival with the track includes associating the initial second angle of arrival with the track only when the initial second angle of arrival does not correspond to a ghost human.

Example 28

A millimeter-wave radar including: first and second receiving antennas configured to receive a reflected radar signal; and a controller configured to: transform the reflected radar signal received with the first and second receiving antennas to generate first and second range spectrum, respectively; generate a first range-Doppler map based on the first range spectrum; generate a second range-Doppler map based on the second range spectrum; determine or estimate a Doppler velocity based on the first range-Doppler map or the second range-Doppler map; compensate the first range-Doppler map and the second range-Doppler map by selecting a peak in the first range-Doppler map or the second range-Doppler map based on the determined Doppler velocity; identify an index of the first macro-compensated range-Doppler map corresponding to an identified target; estimate a phase difference based on the first and second macro-compensated range-Doppler maps and the identified index; and estimate an angle of arrival of the reflected signal based on the phase difference.

Example 29

A method of estimating an angle of arrival of a radar signal reflected on a human target, the method including: transmitting a radar signal towards the human target using a millimeter-wave radar, the transmitted radar signal including a sequence of pulses; receiving the reflected radar signal with first and second antennas of a millimeter-wave radar; determining a range of the human target based on the reflected signal; determining a Doppler velocity of the human target based on the reflected radar signal and the determined range of the human target; generating first and second compensated range-Doppler maps based on the reflected radar signal, the determined range of the human target, and the determined Doppler velocity; identifying an index of the first compensated range-Doppler map corresponding to an identified target; estimating a phase difference based on the first and second compensated range-Doppler maps and the identified index; and estimating the angle of arrival based on the phase difference.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:
1. A method of estimating an angle of arrival of a radar signal reflected on a human target, the method comprising:
receiving a reflected radar signal with first and second antennas of a millimeter-wave radar;
transforming the reflected radar signal received with the first and second antennas to generate first and second range spectrum, respectively;
generating a first range-Doppler map based on the first range spectrum;
generating a second range-Doppler map based on the second range spectrum;
determining or estimating a Doppler velocity based on the first range-Doppler map or the second range-Doppler map using a Fourier transform in slow time;
macro-compensating the first range-Doppler map and the second range-Doppler map by selecting a peak in the first range-Doppler map or the second range-Doppler map based on the determined or estimated Doppler velocity;
identifying an index of the first macro-compensated range-Doppler map corresponding to an identified target;
estimating a phase difference based on the first and second macro-compensated range-Doppler maps and the identified index; and
estimating the angle of arrival based on the phase difference.

2. The method of claim 1, further comprising identifying a set of target range bins based on the first range spectrum, wherein generating the first range-Doppler map is further based on the set of target range bins.

3. The method of claim 2, wherein identifying the set of target range bins is based on an ambiguity function associated with a transmitted radar signal.

4. The method of claim 2, wherein the set of target range bins comprises a plurality of consecutive range bins.

5. The method of claim 2, wherein identifying the set of target range bins comprises performing a peak search on the first range spectrum to generate an identified target range bin.

6. The method of claim 5, wherein the set of target range bins comprises at least three range bins, wherein the three range bins are centered at the identified target range bin.

7. The method of claim 1, wherein generating the first range spectrum comprises:
performing N Fourier transforms on N respective pulses of the reflected radar signal received with the first antenna to generate N range spectra, N being a positive integer greater than 1; and
coherently integrating the N range spectra to generate the first range spectrum.

8. The method of claim 7, wherein N is equal to 16 or 32.

9. The method of claim 7, wherein N corresponds to a total number of pulses within a frame.

10. The method of claim 1, further comprising:
generating a zero-Doppler array based on first or second macro-compensated range-Doppler maps;
determining a vital frequency of a vital sign of a human by selecting a peak of the zero-Doppler array; and
micro-compensating the first and second range-Doppler maps or the first and second macro-compensated range-Doppler maps based on the vital frequency.

11. The method of claim 10, wherein determining the vital frequency comprises performing a Fourier transform in slow time based on the first range-Doppler map.

12. The method of claim 10, wherein the vital sign corresponds to breathing of a human, and wherein the vital frequency corresponds to a breathing frequency of a human.

13. The method of claim 10, wherein determining the vital frequency comprises accumulating zero-Doppler peak values of the first macro-compensated range-Doppler map over a plurality of frames.

14. The method of claim 10, wherein the vital frequency has a frequency lower than 1 Hz.

15. The method of claim 1, further comprising determining a signal-to-noise ratio (SNR) of the identified target in the first range-Doppler map, wherein estimating the angle of arrival comprises updating the angle of arrival associated with the identified target only when the SNR is higher than an SNR threshold.

16. The method of claim 15, further comprising identifying a target range bin by comparing bin values of the first range spectrum with a range threshold, wherein generating the first range-Doppler map is based on the target range bin, and wherein the SNR threshold is based on a range threshold.

17. The method of claim 16, wherein the SNR threshold is substantially equal to 1.2 times the range threshold.

18. The method of claim 1, further comprising transmitting a radar signal towards the human target using the millimeter-wave radar, the transmitted radar signal comprising a sequence of pulses.

19. The method of claim 18, wherein each pulse of the sequence of pulses is a linear chirp.

20. The method of claim 1, wherein identifying the index of the first macro-compensated range-Doppler map comprises performing a two-dimensional peak search of the first macro-compensated range-Doppler map.

21. The method of claim 1, further comprising:
estimating an initial second angle of arrival;
comparing the angle of arrival with the initial second angle of arrival to generate a first difference; and
when a magnitude of the first difference is higher than an angle threshold,
predicting a second angle of arrival based on the angle of arrival and generating a second angle of arrival based on the predicted second angle of arrival, or
avoid generating the second angle of arrival.

22. The method of claim 21, further comprising:
when the magnitude of the first difference is lower than the angle threshold, filtering the initial second angle of arrival to generate a filtered second angle of arrival with a median filter; and
generating the second angle of arrival based on the filtered second angle of arrival.

23. The method of claim 21, further comprising:
when the magnitude of the first difference is lower than the angle threshold, performing conjugative weighting between the predicted second angle of arrival and a value of an angle of arrival based on the initial second angle of arrival to generate a weighted second angle of arrival; and
generating the second angle of arrival based on the weighted second angle of arrival.

24. The method of claim 21, further comprising:
when the magnitude of the first difference is lower than the angle threshold, smoothening a value of an angle of arrival based on the initial second angle of arrival to generate a smoothened second angle of arrival; and
generating the second angle of arrival based on the smoothened second angle of arrival.

25. The method of claim 1, further comprising:
storing location data of an identified target in a memory based on the estimated angle of arrival; and
tracking the location data of the identified target over time, wherein estimating the angle of arrival is further based on the tracked location data.

26. The method of claim 25, further comprising:
estimating an initial second angle of arrival; and
associating the initial second angle of arrival with a track.

27. The method of claim 26, further comprising determining if the initial second angle of arrival corresponds to a ghost human, wherein associating the initial second angle of arrival with the track comprises associating the initial second angle of arrival with the track only when the initial second angle of arrival does not correspond to a ghost human.

28. A millimeter-wave radar comprising:
first and second receiving antennas configured to receive a reflected radar signal; and
a controller configured to:
transform the reflected radar signal received with the first and second receiving antennas to generate first and second range spectrum, respectively;
generate a first range-Doppler map based on the first range spectrum;
generate a second range-Doppler map based on the second range spectrum;
determine or estimate a Doppler velocity based on the first range-Doppler map or the second range-Doppler map using a Fourier transform in slow time;
compensate the first range-Doppler map and the second range-Doppler map by selecting a peak in the first range-Doppler map or the second range-Doppler map based on the determined or estimated Doppler velocity;
identify an index of the compensated first range-Doppler map corresponding to an identified target;
estimate a phase difference based on the compensated first and second range-Doppler maps and the identified index; and
estimate an angle of arrival of the reflected radar signal based on the phase difference.

29. A method of estimating an angle of arrival of a radar signal reflected on a human target, the method comprising:
transmitting a radar signal towards the human target using a millimeter-wave radar, the transmitted radar signal comprising a sequence of pulses;
receiving a reflected radar signal with first and second antennas of the millimeter-wave radar;
determining a range of the human target based on the reflected radar signal;
determining a Doppler velocity of the human target based on the reflected radar signal and the determined range of the human target;
generating first and second compensated range-Doppler maps based on the reflected radar signal, the determined range of the human target, and the determined Doppler velocity;
identifying an index of the first compensated range-Doppler map corresponding to an identified target;
estimating a phase difference based on the first and second compensated range-Doppler maps and the identified index;
estimating the angle of arrival based on the phase difference;
estimating an initial second angle of arrival;
comparing the angle of arrival with the initial second angle of arrival to generate a first difference; and
when a magnitude of the first difference is higher than an angle threshold,
predicting a second angle of arrival based on the angle of arrival and generating a second angle of arrival based on the predicted second angle of arrival.

30. The method of claim 29, further comprising, when the magnitude of the first difference is lower than the angle threshold:
performing conjugative weighting between the predicted second angle of arrival and a value of an angle of arrival based on the initial second angle of arrival to generate a weighted second angle of arrival;
smoothening the weighted second angle of arrival to generate a smoothened second angle of arrival; and
generating the second angle of arrival based on the smoothened second angle of arrival.

31. The millimeter-wave radar of claim 28, wherein the controller is further configured to:
  estimate an initial second angle of arrival;
  compare the angle of arrival with the initial second angle of arrival to generate a first difference; and
  when a magnitude of the first difference is higher than an angle threshold,
    predict a second angle of arrival based on the angle of arrival and generating a second angle of arrival based on the predicted second angle of arrival, or
    avoid generating the second angle of arrival.

* * * * *